United States Patent [19]
Proba et al.

[11] Patent Number: 5,506,127
[45] Date of Patent: Apr. 9, 1996

[54] THERAPEUTIC GRADE THROMBIN PRODUCED BY CHROMATOGRAPHY

[76] Inventors: Zbigniew Proba; Teresa Brodniewicz, both of 3067 Murray Avenue, Chomedey, Laval, Quebec, Canada, H7V 2H2

[21] Appl. No.: 309,583

[22] Filed: Sep. 21, 1994

[51] Int. Cl.⁶ ............................................. C12N 9/74
[52] U.S. Cl. ................................. 435/214; 435/815
[58] Field of Search ............................. 435/214, 815; 530/344

[56] References Cited

U.S. PATENT DOCUMENTS

| | | | |
|---|---|---|---|
| 4,083,957 | 4/1978 | Lang | 424/78 |
| 4,202,872 | 5/1980 | Collen | 424/78 |
| 4,380,511 | 4/1983 | Mannuzza et al. | 260/112 B |
| 4,540,573 | 9/1985 | Neurath et al. | 424/85 |
| 4,696,812 | 9/1987 | Silbering et al | 424/445 |
| 4,923,815 | 5/1990 | Tanaka et al. | 435/183 |
| 4,965,203 | 12/1990 | Silbering et al. | 435/188 |
| 5,130,244 | 7/1992 | Nishimaki et al. | 435/188 |
| 5,143,838 | 9/1992 | Kraus et al. | 435/214 |
| 5,149,540 | 9/1992 | Kunihiro et al. | 424/489 |
| 5,151,355 | 9/1992 | Crowley et al. | 435/214 |
| 5,229,172 | 7/1993 | Cahalan et al. | 427/536 |
| 5,331,092 | 7/1994 | Huc et al. | 530/356 |
| 5,354,682 | 10/1994 | Kingdon et al. | 433/214 |
| 5,397,704 | 3/1995 | Boctor et al. | 435/214 |

FOREIGN PATENT DOCUMENTS

| | | |
|---|---|---|
| 0378798 | 7/1990 | European Pat. Off. . |
| 1443724 | 8/1991 | European Pat. Off. . |
| 3809991 | 10/1988 | Germany . |
| 1527261 | 3/1988 | U.S.S.R. . |

OTHER PUBLICATIONS

*Ann. pharmaceutique francaise* 48 (part 3):129–135, 1990.

Primary Examiner—David M. Naff
Assistant Examiner—Michael V. Meller
Attorney, Agent, or Firm—Hoffman, Wasson & Gitler

[57] ABSTRACT

A process for the large-scale production of therapeutic grade thrombin of excellent viral safety and storage-stability is carried out by purification of viricide treated crude thrombin by ion-exchange chromatography on a single column using a sulfalkyl-activated polysaccharide, particularly a non-compressible composite medium of sulfoalkyl-activated dextran and silica particles, as the ion exchange medium and using increasing concentrations of phosphate buffer for elution. After recovery of thrombin in the final eluate, the phosphate buffer is exchanged for a stabilizing formulation buffer, and the stabilized thrombin is subjected to viral filtration and optional dry heat treatment for further viral inactivation. The final product has high specific activity and is obtained in good yield.

13 Claims, No Drawings

THERAPEUTIC GRADE THROMBIN PRODUCED BY CHROMATOGRAPHY

BACKGROUND OF THE INVENTION

1. Field of the Invention

The invention relates to therapeutic grade thrombin products for clinical (including veterinary) use. The thrombin is characterized by high viral safety, high specific activity, storage-stability, and low pyrogenicity. The invention further relates to methods for preparing the thrombin products which are efficient, economical, and well-suited to commercial-scale production.

Thrombin is widely used in clinical applications as a coagulation factor to staunch bleeding of wounds by conversion of fibrinogen to fibrin. It is a common component of surgical dressings, and has been used in combination with fibrinogen and other coagulation proteins in two-component hemostatic systems such as fibrin glues, adhesives, and sealants. Both human and bovine plasma are recognized as a source of thrombin for human clinical use. However, largely because of the difficulty of purifying thrombin from non-autologous human plasma with substantial removal or inactivation of any viruses which may be present in the starting plasma, therapeutic grade thrombin products for human use which are generally commercially available are derived from bovine plasma which has a low inherent potential for harboring viruses inimical to humans, notwithstanding the well-recognized immunogenic potential of bovine thrombin in humans which is of considerable clinical concern.

For clinical use, thrombin is typically derived from blood plasma as a protein complex with prothrombin, usually followed by conversion of the proenzyme to thrombin by reaction with thromboplastin in the presence of calcium ions. The crude thrombin product is then processed to separate thrombin from contaminating blood proteins and to inactivate or remove any toxins or pathogens which may be present. Ideally, the recovered product is a therapeutic grade thrombin (thrombin conforming to USFDA standards for human use) which has a high specific activity, good storage-stability, low pyrogenicity, and which is substantially virus-free.

This ideal is rarely, if ever, met. In purification methods in general use for obtaining therapeutic grade thrombin, recovery of highly pure thrombin is typically accomplished at the expense of significant amounts of active thrombin through loss or inactivation of thrombin in the starting material during purification. In less pure products, the presence of extraneous plasma proteins (whether bovine or non-autologous human proteins) increases the risk of possibly severe immunological reactions in the patient and typically adversely affects the properties of the product. In particular, current purification processes generally permit only a very limited amount of plasma purification with respect to vital contaminants without unacceptable loss of thrombin activity. Furthermore, many thrombin purification processes reported to be relatively effective in laboratory settings to provide therapeutically-attractive thrombin products do not lend themselves to economical large-scale commercial production. As a result, thrombin products which have been proposed for human clinical use variously present a significant toxic risk, are not consistently highly efficacious, and/or require complex preparation methods not adaptable to large-scale production. Additionally, known purification processes or the products thereof lack versatility: for example, the products as a practical martex are generally not applicable to veterinary practice, and the processes are too complex or ineffective for use in a clinical setting for autologous plasma purification.

2. Discussion of Related Art

Thrombin is conventionally purified from the crude thrombin product by chromatography employing as separation media various ion exchange polymers, particularly activated polysaccharides such as agarose, dextran, or cellulose. To obtain a thrombin product having an adequately high specific activity from the crude thrombin staxting material, multi-stage chromatographyusing alternating anion and cation exchange media is typically employed, for example, DEAE (diethylaminoethyl) Sepharose® as anion exchange medium and CM- or S- Sepharose® as cation exchange medium (see, e.g., U.S. Pat. No. 5,149,540 to Kunihiro et al., issued Sep. 22, 1992 or U.S. Pat. No. 4,965,203 to Silbering, et al., issued Oct. 23, 1990). These multiple chromatography steps are time-consuming, increase the cost of the process, and often are not adaptable to large scale production of therapeutic grade thrombin.

As known in the art, thrombin may be treated in the course of the purification procedure to inactivate lipid-containing virions with a solvent-detergent (SD) composition comprising a nonionic detergent and an organic solvent capable of disrupting viral lipids and inactivating the virus without denaturing thrombin. While such purified thrombin products are sometimes characterized as "virus free" (see, e.g., EP 0 443 724 A1, published Aug. 28, 1991), they are often not. While SD treatment of the thrombin-containing material is generally effective to inactivate enveloped virions, non-enveloped virions such as parvoviruses are not inactivated by this procedure, and any such virions present in the starting material may be carried through the purification process and remain active in the final thrombin product, presenting a clinical hazard. While this problem has been recognized, it has been difficult to solve, as other standard methods for rizal inactivation such as heat or UV treatment also inactivate thrombin, with unacceptable loss of active thrombin for commercial applications.

SUMMARY OF THE DISCLOSURE

The invention accordingly provides in good yield a storage-stable therapeutic grade thrombin concentrate of high specific activity and low pyrogenicity, substantially purified with respect to virions. The purification process includes the steps of 1) incubation of crude thrombin starting material with a viricide composition to inactivate lipid-containing enveloped virions; 2) sequential ion exchange chromatography of the incubated material on a single cation exchange medium, using increasing concentrations of phosphate buffer and a sulfalkyl-activated polysaccharide medium such as agarose, dextran, cellulose having a high selective affinity for thrombin, with recovery of a final eluate comprising a phosphate buffer solution of thrombin highly purified with respect to contaminants including other blood proteins, toxins, lipid-containing enveloped virions, and viricide residue; 3) exchange of the phosphate chromatography buffer of the final eluate for a physiologically-compatible formulation buffer to provide a formulation solution of highly purified thrombin; 4) filtration of the thrombin formulation solution over a vital filter to remove non-lipid containing virions; and 5) optional dry heat treatment of filtered and lyophilized thrombin to ensure inactivation of any possible remaining virions (infective vital materials).

Aqueous saline formulation buffers of a pH of about 7.2 to 7.4 comprising a citric acid salt and 1) bovine albumin for bovine thrombin intended for veterinary applications, and 2) human albumin for bovine and human thrombin intended for human applications are exemplary. The formulation solutions of the invention (described in more detail below) broadly contribute, inter alia, to stabilization of thrombin enzymatic activity during post-chromatography treatment and during storage; the used formulation also stabilize thrombin against loss of activity during antiviral dry heat treatment according to step (5).

The product is a storage-stable therapeutic-grade thrombin of high vital safety and specific activity for general clinical use, including veterinary use. The high specific activity coupled with good product yield reflects the efficiency of the process for purifying crude thrombin with respect to contaminating proteins, other extraneous and potentially toxic starting material components, viricide residues, and virions without substantial loss or inactivation of starting thrombin. Viricide residues of less than about 15 ppm are typically obtainable. Product stability against significant loss of activity for at least a year under storage at about 4° C. has been obtained. The process is applicable to thrombin from any useful source, particularly human and bovine, and is particularly useful for large-scale production of therapeutic grade thrombin. For applications wherein substantially complete viral safety of the product is not required, or where vital safety is otherwise not considered a problem, vital filtration and heat treatment (steps 4 and 5) may be omitted.

DETAILED DESCRIPTION OF THE INVENTION

In an exemplary embodiment of the invention for human clinical use, a crude human thrombin preparation is first incubated with a lipid-disrupting viricide to inactivate lipid-containing virions. The treated preparation is then sequentially purified by ion exchange chromatography using sulfopropyl-Spherodex® as the sole adsorption medium and increasing concentrations of phosphate buffer in each passage to obtain a final eluate comprising a concentrated solution of thrombin substantially purified with respect to active lipid-containing virions, contaminating proteins, and viricide residues. To the collected thrombin peak solution, stabilizing albumin is added and then the chromatography buffer is exchange for a formulation buffer solution by diafiltration. The resulting thrombin formulation solution comprising the formulation buffer components, albumin, water, and purified thrombin is then filtered to remove non-lipid-containing virions. The viral-purified thrombin is then diluted to the required concentration in formulation buffer, final concentration of stabilizing albumin is adjusted to 2% and the solution is sterile filtered, lyophilized, and stored at about 4° C. To ensure a virion-free product the viral-filtered, lyophilized thrombin is subjected to a dry heat treatment at about 100° C. to inactivate any remaining active viruses.

Crude Thrombin Preparation

Any suitable preparation containing thrombin can be used as starting material for the process of the invention, including commercially-obtained preparations. The present invention makes the safe use of human plasma as a source of thrombin practicable, and for human clinical use, human plasma is accordingly generally preferred, as this reduces the risk of allergic reactions in the recipient. Bovine plasma is a generally preferred starting material for thrombin products according to the invention for veterinary use. As known in the art, crude thrombin is obtainable from acidified fresh plasma, cryosupernatant, supernatant after salt precipitation, or any other plasma fraction containing this protein. An exemplary process for preparing a starting crude thrombin material useful in the present invention is described in *Ann. pharmaceutique francaise* 48 (part 3):129–135, 1990. Broadly, the reported process comprises dilution of the starting plasma or plasma fraction with distilled wares to reduce salt concentration to below about 10% of the original fresh plasma concentration with adjustment of the pH of the diluted solution to about 5.3; centrifugation of the solution to obtain a precipitate containing crude prothrombin; dissolving the precipitate in NaCl solution with adjustment of pH to about 7.0; and addition of calcium ions to the resultant solution with incubation for at least about 2 hours at room temperature to convext prothrombin to thrombin. The thrombin solution is then centrifuged to provide a supernatant containing crude thrombin suitable for use as a starting material for the invention; the supernatant is then mixed with viricide as described below, and the precipitate discarded. In a preferred embodiment, particularly useful for large-scale production of thrombin, the above-described process is improved according to the present invention by using diafiltration, especially diafiltration employing an about 0.015M NaCl solution instead of water as replenishment buffer, to seduce salt concentration of the starting plasma while retaining about the original volume of material; the diafiltration may comprise either constant volume ultrafiltration with continuing addition of fresh buffer, or repeated ultrafiltration with addition of fresh buffer after each concentration cycle. This effectively reduces the salt concentration of the staxting plasma to the desired level, while avoiding the very large increase in volume of material to be centrifuged to obtain a crude prothrombin precipitate resulting from dilution according to the prior art.

Viricide

Any suitable viricide for inactivation of lipid-containing viruses as known in the art may be employed; compositions comprising a nonionic detergent such as a Tween® or Span® series polyoxyethylenesorbitan detergent and/or organic solvent such as a di- os tri-alkyl phosphate which disrupts viral lipids and inactivates lipid-containing virions without significant denaturation of thrombin, are currently recommended. Such viricide compositions are broadly referred to herein as "solvent-detergent" or SD compositions. SD compositions comprising a di- or tri- alkylphosphate optionally in combination with a nonionic detergent as wetting agent and/or alcohol ether, incubated with the contaminated protein as described in U.S. Pat. No. 4,540,573 issued Sep. 10, 1985 to Neurath, et al. (incorporated herein by reference) are exemplary. According to the process of the present invention, the selected solvent-detergent composition is incubated with the crude thrombin starting material psior to chromatography, with removal during chromatography (below) of viricide residues and contaminants, particularly other coagulation factors, contained in the starting material. A preferred non-denaturing SD composition for use according to the invention is based on a $C_2$-$C_{10}$-trialkylphosphate such as tri-n-butylphosphate and a polyoxyalkylene derivative of a sorbitol/fatty acid partial ester such as Tween 80® (polyoxyethylenesorbitan monooleate) at a physiological pH.

Ion Exchange Purification

According to the invention, the viricide-treated starting crude thrombin material is purified by sequential column chromatography using a single adsorption medium with increasing concentrations of buffer in each run. Useful chromatography parameters are well-known in the art; an improved process according to the present invention comprises sunning the chromatographic separation at a temperature of about 12° C., rather than conventionally at room temperature (about 20° C.), which significantly increases yields. The chromatographic purification of thrombin from crude thrombin starting material incubated with viricide is described herein in terms of column chromatography; however any other comparable physical arrangement such as cartridges for contacting the adsorption medium with the thrombin preparation may be employed. By the process of the invention, the ion exchange purification process provides a thrombin product of high specific activity and good yield, reflecting the highly efficient and effective purification of the crude thrombin with respect to extraneous materials in the crude preparation, particularly other blood proteins or bacterial toxins, and viricide residues.

A. Adsorption media.

Any cation exchange adsorption media suitable for separation of thrombin from the crude, viricide-treated staxting material to provide a therapeutic grade product may be employed, especially media highly selective for thrombin such as S-Sepharose® or SP-Sephadex®, commercially available from Sigma Chemical Co., St. Louis, Mo., USA. In an embodiment of the present invention which is particularly preferred for large-scale production, sulfopropyl-Spherodex® gel (available from Sepracor Inc., Marlborough, Mass., USA) is employed as the ion exchange medium. This medium is a non-compressible composite rigid gel comprising silica particles covered uniformly with the sulfopropyl activated dextran which has both high capacity for thrombin adsorption and excellent flow properties, permitting fast and efficient purification. Also, the medium is quickly and conveniently renewed after use by washing with e.g., sodium hydroxide solution for both sanitation and removal of proteins or other materials from the column. In general, non-rigid gels such as SP-Sephadex and comparable gels are not recommended for large scale purification of thrombin according to the present invention, as it has been found that significantly reduced flow rates during thrombin purification according to the invention are caused by compression of the column due to the flexibility of these media. The final chromatography eluate comprises a bovine thrombin composition having a specific activity of at least about 2000 NIH units per mg native protein (i.e., not including any added protein such as stabilizing serum albumin, see below) at a yield of at least 70% up to about 90% bovine thrombin (at least about 265,000 NIH units bovine thrombin up to about 340,000 units, starting from 6 grams of commercial crude thrombin of specific activity 100 NIH/mg) os a human thrombin composition having a specific activity of at least about 1000 NIH units per mg native protein (i.e., not including any added protein such as stabilizing serum albumin, see below) obtained with a yield of at least about 70% up to about 90% human thrombin (at least about 150,000 NIH units human thrombin up to about 180,000 units, starting from 5 l of plasma supernatant after salt precipitation. 20% loss of activity during the S/D treatment and batch to batch variations is included in the given units range).

B. Chromatography Buffer

The chromatography buffer comprises an aqueous phosphate solution comprising $KH_2PO_4/Na_2HPO_4$ (for bovine thrombin) and $KH_2PO_4/K_2HPO_4$ (for human thrombin); the components of the individual buffer solutions are admixed with (preferably distilled) water in substantially equimolar proportions and then monobasic and dibasic phosphate solutions are mixed in proportions providing a final buffer solution having a pH of substantially 6.5 for bovine thrombin and 6.35 for human thrombin. The column is first equilibrated with a low concentration of phosphate buffer (about 0.025M), and washed with increasing concentrations of the same buffer until all UV absorbing material is eluted. The final eluate (thrombin peak solution) is recovered and viral-treated as described below for viral safety as appropriate to the intended application. For bovine thrombin, the column is preferably washed with three increasing concentrations of the buffer (about 0.025M, 0.3M, and 0.4M); the third washing with 0.4M buffer elutes the thrombin peak solution. viricidal residues and contaminating proteins are removed during the first two washings. Fox human thrombin, the column is preferably washed with three increasing concentrations of buffer (about 0.025M, 0.18M, and 0.25M); the third washing with 0.25M buffer elutes the thrombin peak solution. Viricidal residues and contaminating proteins are removed during the fixst two washings.

Buffer Exchange

Recovered thrombin peak solution from above is diafiltered or otherwise treated according to known methods to exchange the chromatography buffer solution for formulation buffer solution. Any formulation buffer solution in which thrombin is soluble and which stabilizes the thrombin solution against the described subsequent process steps for the intended application can be used, especially solutions of Tris-HCl (about 0.20 to 0.30 w/w % of the total composition) in aqueous saline (about 0.40 to about 0.50 w/w % NaCl of the total composition). Particularly good results according to the present invention for stabilizing thrombin against post-chromatography viricidal treatment and storage degradation are obtained for example by employing a formulation buffer solution comprising an aqueous solution of about 0.25% sodium citrate, 0.45% sodium chloride, 0.25% Tris-HCl (all w/v %); pH 7.3.

For best results, bovine or human serum albumin (according to the intended use) is preliminary added to the thrombin peak solution before exchange of chromatography buffer with the formulation buffer solution, in amount of about 20 times total solution protein (i.e., "native protein") on a wt % basis. The final concentration of albumin is increased to 2% (w/v) after the thrombin solution is diluted to required concentration at the end of the process just before filling. To exchange buffers, the recovered thrombin peak solution is preferably diafiltered, using, for example, a volume of formulation buffer equal to about 8 times the volume of the thrombin peak solution and a 30,000 mw cut-off membrane or other convenient membrane which zetains thrombin (mw 36,000, varying slightly according to source), and albumin (mw 66,000, varying slightly according to source), but not smaller proteins. While improved results may be obtained by addition of the albumin (or, less preferably at the present time, any other stabilizing protein) at any time prior to storage, it is preferred that the albumin be included in the formulation solution before it is exchanged for the chromatography buffer solution, as the albumin contributes to stabilization of the thrombin during all the post-chromatography steps. As described above, it is most preferred that the albumin be added to the thrombin peak solution before the buffer exchange step. Suitable serum albumin for use in the practice of the invention is generally commercially available; for example, a useful human serum albumin comprises Plasbumin-25® (Miles Canada Inc., Etobicoke, Ontario, Canada), comprising a USP 25% albumin solution additionally containing two stabilizers: 0.02M acetyltryptophan and 0.02M sodium caprylate, with no preservatives, made from pooled human venous plasma using the Cohn cold ethanol fractionation process and heat treated at 60 degrees C for 10 hours against the possibility of transmittal of hepatitis viruses. In an preferred step according to the present application, about 10 ml of albumin solution is fixst added to about 500 ml thrombin peak solution, followed by diafiltration of the albumin-modified peak solution with about 8 times volume of formulation burrex for buffer exchange. By this step, at least about 99%, more usually about 99.99% of low molecular weight contaminants are exchanged by the formulation buffer, leaving inside all proteins larger than the molecular weight cutoff capacity of the diafiltration membrane. Preferably, human serum albumin is used for both human and bovine thrombin intended for human applications and bovine serum albumin is used for bovine thrombin intended for veterinary applications.

Depending upon the intended use, the purified thrombin product in formulation buffer from above may be used as is after final formulation, sterile filtration, and lyophilization, particularly purified bovine thrombin for veterinary use. For human applications, the product is preferably subjected to further viral purification as follows:

Viral Filtration

To further purify thrombin with respect to non-lipid containing viruses, the recovered thrombin in formulation buffer, preferably including serum albumin os other stabilizing protein, is filtered over a hollow-fibre membrane such as a BMM microporous membrane (Bemberg Microporous Membrane BMM Development, Asahi Chemical Industries) comprising a cuprammonium regenerated cellulose fiber having a pose size of about 15 nm, of the type manufactured by Asahi Chemical Industries, Tokyo, Japan, and sold under the trademark Planova BMM. This technique substantially removes non-lipid containing virions which cannot be inactivated by the SD treatment of the process. The filter is particularly suitable for thrombin purification, as it can handle a high concentration of thrombin at a low volume of solution: for example, starting from 5 liters human plasma, volume of about 125 ml of obtained purified thrombin solution (600–800 NIH/ml) was filtered using 0.01 sq. m., 15 nm Planova BMM filter. Under those conditions, the tested rate of removal of small polio virus was more than 7 logs.

Dry Heating

While the described SD treatment removes typically between 4 and 6 logs of lipid containing enveloped viruses and the 15 nm viral filtration between 4 and 8 logs of any surviving SD treatment small viruses, to ensure viral safety, the thrombin preparations lyophilized in vials, may be additionally subjected to a dry heat treatment at about 100° C. for about 1 hour to 2 hours. Low moisture content of the product during the treatment is important to avoid unnecessary deactivation of thrombin.

EXAMPLES

Example I

Solvent-detergent treated bovine thrombin production.

Six grams of crude commercial bovine thrombin (obtained from GenTrac, Inc., Middleton, Wisc., USA) having a specific activity of 100 NIH was dissolved in 75 ml of aqueous buffer containing 1% Tris-HCl and 1.62% sodium citrate (all w/v %), pH 7.0. 75 ml of aqueous solvent-detergent solution was added (1% Tris-HCl, 1.62% NaCitrate, 2% Tween 80®, 0.6% tri-n-butylphosphate (TnBP), all w/v %; pH 7.0) and the mixture was stirred for 6 hrs at 25° C.

The mixture was directly applied to a sulfopropyl-Spherodex column (2.5 cm×13 cm, Pharmacia) equilibrated with 0.025M $KH_2PO_4/Na_2HPO_4$ in aqueous solution (prepared as described above), at pH 6.5. The column was washed with three increasing concentrations of this buffer (0.025M, 0.3M, and 0.4M, all at DH 6.5) until all UV absorbing material was eluted. The material eluted with the 0.025M and 0.3M buffers contained SD mixture components and contaminating proteins and was discarded. The third elution with 0.4M buffer contained purified, solvent-detergent antiviral treated bovine thrombin of specific activity greater than 2,000 NIH units per mg protein, with a 70 to 90% yield. Purification was performed at 12° C. Bovine serum albumin was added to the collected thrombin peak solution in an amount equal to 20 times total protein, and the resulting solution was subjected to 8 times volume diafiltration using a 30,000 molecular weight cut-off membrane (Amicon YM 30 membrane, Amicon Division, W. R. Grace & Co.-Conn., Beverly, Mass., USA), with exchange of the chromatography buffer for the following formulation buffer: 0.25% sodium citrate, 0.45% sodium chloride, 0.25% Tris-HCl (tris(hydroxymethyl)aminomethane hydrochloride) (all amounts in w/v %), in aqueous solution at pH 7.3. After diafiltration the thrombin solution was diluted to a concentration of 220 NIH/ml with the same formulation buffer, the bovine serum albumin content was increased to 2% and the solution was sterile filtered, filled into vials and lyphollized. The vials were stored at 4 degrees C. Prior to addition of serum albumin, thrombin specific activity was greater than 2,000 NIH/mg protein. SD residue present in the final product reconstituted in 1 ml of water was: Tween 80<15 ppm; TnBP<15 ppm. Vials were each filled with 220 NIH units of the bovine thrombin. Accelerated stability studies at 37° C. for 2 months (corresponding to 6 months at 4° C.) showed no significant loss of thrombin activity.

Example II

Double antiviral treated human thrombin.

Five liters of human plasma fraction, left after salt precipitation of coagulation proteins used in the production of fibrin sealant, was processed according to the procedure described in *Ann. pharmaceutique francaise,* op.cit., supra., using a diafiltration step rather than the reported dilution procedure, as described above. Starting plasma fraction was diafiltered with 0.015M NaCl aqueous solution concentration to about 10% of the original concentration in fresh plasma, and the pH adjusted to 5.3 with 2% acetic acid and the mixture was stirred for 30 min. at room temperature. The material was then centrifuged for 20 min. at 4,200 rpm, and the resulting precipitate dissolved in 250 ml of 0.9% NaCl per liter of plasma with adjustment of the pH to 7.0 with 2% sodium carbonate. Prothrombin was convexted to thrombin by addition of calcium chloride to obtain a final concentration of 21 nM, followed by incubation at room temperature for 2 hrs and centrifugation at 4,200 rpm for 20 min. 200,000–250,000 NIH units of crude thrombin was obtained from 5 l of starting plasma fraction.

The protein concentration of the crude thrombin preparation was adjusted to about 10–15 mg/ml, and the solution was subjected to solvent-detergent antiviral treatment by adding an equal volume of the following SD composition: aqueous solution of 1% Tris-HCl, 1.62% sodium citrate, 2% Tween 80® (Sigma Chemical Co.), and 0.6% tri-n-butylphosphate (all w/v %) with stirring for 6 hrs at 25° C.

After incubation, the crude thrombin material was applied directly to a sulfopropyl-Spherodex column (5 cm×13 cm, Pharmacia) equilibrated with 0.025M $KH_2PO_4/K_2HPO_4$ at pH 6.35. The column was washed with four increasing concentrations of phosphate buffer (below) until all UV absorbing material was eluted.

The material eluted with the fixst two buffers (0.025M and 0.18M) contained SD mixture components and contaminating proteins, and was discarded. The third elution with 0.25M buffer contained purified SD antiviral treated human thrombin of specific activity 1200 NIH units per mg protein obtained with 90% yield. To the collected thrombin peak solution a solution of human serum albumin approved for human use (plasbumin-25®) was added in an amount equal to 20 times (by weight) of total protein present in the thrombin peak solution, and the solution was subjected to 8 times volume diafiltration using a 30,000 molecular weight cut-off membrane and the following sterile formulation buffer: 0.25% sodium citrate, 0.45% sodium chloride, 0.25% Tris-HCl (all w/v %) in aqueous solution, pH 7.3.

The thrombin solution then was antiviral filtered using a 0.01 sq.m (filtration asea) 15 nm (pose size) Planova BMM filter (Asahi Chemical Co., above), and 10 psi pressure. The filtered thrombin was diluted to the required concentration (in this case 220 NIH/ml) with the same sterile formulation buffer, the human albumin concentration was increased to 2%, the solution was sterile filtered, filled into vials, lyophilized, and stored at 4° C. The vials were filled with 200 NIH units of bovine thrombin and accelerated stability studies were done at 37° C. for 2 months, corresponding to 6 months at 4° C. No significant loss of thrombin activity was observed (as measured by standard clotting methods). Therefore, specific activity of the product was maintained during storage.

Example III

Triple antiviral treated human thrombin.

The vials containing lyophilized human thrombin were subjected to heating at 100° C. for 1 to 2 hrs. No loss of thrombin activity was observed.

The procedures exemplified in Examples I, II and III are readily scaled up for commercial production.

What is claimed is:

1. A process for the large-scale production of a storage-stable therapeutic grade thrombin composition substantially free from lipid-containing viruses comprising:
   a) incubating crude thrombin with a viricide for lipid-containing viruses in an amount sufficient to inactivate these viruses if present;
   b) purifying the incubated material by sequential ion-exchange chromatography using a single sulfalkyl-activated polysaccharide cation exchange medium selected from the group consisting of a sulfalkyl-activated polyagarose, a sulfalkyl-activated polydextran and a noncompressible composite medium of sulfalkyl-activated dextran and silica particles having a high selectivity for thrombin using as an eluting agent at least three and increasing concentrations of an aqueous buffer solution consisting essentially of $KH_2PO_4$ and the sodium or potassium salt of $HPO_4$ having a pH of about 6.5 as the eluting agent for bovine thrombin and a pH of about 6.35 for human thrombin; and
   c) recovering thrombin peak eluate from the chromatography, of b) and exchanging the buffer of the eluate with a physiologically compatible stabilizing formulation buffer for stabilizing the recovered thrombin and recovering a formulation buffer solution of thrombin.

2. The process of claim 1, wherein the cation exchange medium is said non-compressible composite medium of sulfoalkyl-activated dextran and silica particles.

3. The process of claim 2, wherein the cation exchange medium is a substantially non-compressible composite medium of sulfopropyl-activated dextran and silica particles.

4. The process of claim 1, further including filtering the thrombin formulation buffer solution over a hollow fiber cuprammonium cellulose membrane to filter out visions present in the formulation buffer solution, and recovering a substantially virion-free formulation buffer solution of thrombin.

5. The process of claim 1, further including lyophilization and dry heat treatment of the thrombin formulation buffer solution after filtration to inactivate any remaining visions without denaturation of thrombin.

6. The process of claim 4, further including lyophilization and dry heat treatment of the thrombin formulation buffer solution after filtration to inactivate any remaining visions without denaturation of thrombin.

7. The process of claim 5, wherein the formulation buffer solution comprises an aqueous solution of citrate salt, sodium chloride, Tris-HCL, and serum albumin at a pH of about 7.3, in amounts sufficient to stabilize the thrombin against substantial loss of activity during heat treatment.

8. The process of claim 6, wherein the formulation buffer solution comprises an aqueous solution of citrate salt, sodium chloride, Tris-HCL, and serum albumin at a DH of about 7.3, in amounts sufficient to stabilize the thrombin against substantial loss of activity during heat treatment.

9. The process of claim 1, wherein the crude thrombin is bovine thrombin, and the thrombin product has a specific activity of at least about 2000 NIH units/mg native protein and a viricide residue of less than about 15 ppm.

10. The process of claim 1, wherein the crude thrombin is human thrombin, and the thrombin product has a specific activity of at least about 1000 NIH units/mg native protein and a viricide residue of less than about 15 ppm.

11. The process of claim 7, wherein the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

12. The process of claim 8, wherein the formulation buffer solution comprises an aqueous solution of about 0.25% sodium citrate, 0.45% sodium chloride, 0.25% Tris-HCl, all w/v %; serum albumin in an amount about equal to about 20 times the total protein in the thrombin peak eluate and adjusted before lyophilization to 2% w/v; and having a pH of about 7.3.

13. The method of claim 1, wherein the increasing buffer concentrations consist essentially of about 0.025M, 0.3M, and 0.4M buffer for bovine thrombin and about 0.025M, 0.18M, and 0.25M buffer for human thrombin.

* * * * *